(12) United States Patent
Berg et al.

(10) Patent No.: US 7,478,702 B2
(45) Date of Patent: Jan. 20, 2009

(54) CUSTOMIZED HEARING PROTECTION EARPLUG AND METHOD FOR MANUFACTURING THE SAME

(75) Inventors: Christian Berg, Uerikon (CH); Gregory Bleiker, Herrliberg (CH); Mathias Haussmann, Zurich (CH)

(73) Assignee: Phonak AG, Staefa (CH)

( * ) Notice: Subject to any disclaimer, the term of this patent is extended or adjusted under 35 U.S.C. 154(b) by 360 days.

(21) Appl. No.: 11/019,614

(22) Filed: Dec. 23, 2004

(65) Prior Publication Data

US 2006/0042868 A1    Mar. 2, 2006

Related U.S. Application Data

(63) Continuation-in-part of application No. 10/925,144, filed on Aug. 25, 2004, and a continuation-in-part of application No. 10/925,138, filed on Aug. 25, 2004.

(51) Int. Cl.
    *H04R 25/02* (2006.01)
(52) U.S. Cl. .................. 181/135; 181/129; 181/130; 381/322; 381/324; 381/328; 381/329
(58) Field of Classification Search ............ 181/129, 181/130, 135; 381/322, 324, 328, 329
    See application file for complete search history.

(56) References Cited

U.S. PATENT DOCUMENTS 4,133,984 A * 1/1979 Akiyama ............... 381/328
4,539,440 A * 9/1985 Sciarra .................. 381/329
4,871,502 A * 10/1989 LeBisch et al. ......... 264/222
4,913,165 A * 4/1990 Fishgoyt ................ 128/865
6,006,857 A * 12/1999 Leight et al. ........... 181/135
6,129,174 A * 10/2000 Brown et al. ........... 181/135
6,148,821 A   11/2000 Falco
6,484,842 B1 * 11/2002 Widmer et al. .......... 181/129
6,533,062 B1   3/2003 Widmer et al.
6,671,381 B1 * 12/2003 Lux-Wellenhof ........ 381/325
2002/0006209 A1 * 1/2002 Mahoney et al. ......... 381/322
2002/0025055 A1 * 2/2002 Stonikas et al. ......... 381/322
2002/0080979 A1 * 6/2002 Brimhall et al. ......... 381/72
2003/0133583 A1   7/2003 Widmer et al.
2004/0258263 A1 * 12/2004 Saxton et al. ........... 381/328

FOREIGN PATENT DOCUMENTS

AU        56067 73 A    11/1974
DE        268345 C      12/1913

(Continued)

*Primary Examiner*—Edgardo San Martin
*Assistant Examiner*—Jeremy Luks
(74) *Attorney, Agent, or Firm*—David S. Safran; Roberts Mlotkowski Safran & Cole, P.C.

(57) ABSTRACT

The invention relates to a hearing protection earplug (10) to be worn at least in part in a user's ear canal, comprising a shell (12) having a outer surface individually shaped according to the measured inner shape of the user's outer ear and ear canal, and a functional member (20, 30, 120, 144, 220, 320, 420) engaging said shell in a manner so as to be movable relative to said shell between a first functional position and a second functional position, said shell and said functional member having been produced by an additive layer-by-layer build-up process and having an elasticity of between shore D85 and D65.

18 Claims, 6 Drawing Sheets

FOREIGN PATENT DOCUMENTS

| | | |
|---|---|---|
| WO | WO 95/15067 A1 | 6/1995 |
| WO | WO 96/40479 A1 | 12/1996 |
| WO | WO 98/25558 A1 | 6/1998 |
| WO | WO 01/13840 A1 | 3/2001 |
| WO | WO 02/24129 A1 | 3/2002 |
| WO | WO 02/071794 A1 | 9/2002 |

* cited by examiner

CUSTOMIZED HEARING PROTECTION EARPLUG AND METHOD FOR MANUFACTURING THE SAME

BACKGROUND OF THE INVENTION

1. Field of the Invention

The present invention relates to a hearing protection earplug comprising a shell having an outer surface individually shaped according to the measured inner shape of the user's outer ear and ear canal and a functional member engaging the shell, wherein the shell is produced by an additive layer-by-layer build-up process and has an elasticity of between shore D85 and D65. The invention also relates to a corresponding manufacturing process.

2. Description of Related Art

Earplugs comprising a customized shell, i.e. a shell having an outer surface individually shaped according to the measured inner shape of the user's outer ear and ear canal, with the shell being produced by an additive layer-by-layer build-up process, are known for example from U.S. 2003/0133583 A1, according to which a shell produced by an additive layer-by-layer laser sintering of a powder material is provided with functional elements, such as component mounts and holders, cerumen-protection systems, venting channels or channel locks which keep the earplug in place in the ear canal, may be integrated directly within the customized shell. These functional elements include holders or receptacles for electronic components necessary for hearing aid devices.

Similar earplugs are described in WO 02/071794, according to which a customized shell produced by an additive layer-by-layer build-up process is adapted to receive additional components such as electronic components, battery devices, outlet to interior components, tubes, transducers and logos.

Further, it is known to provide earplugs with movable elements which are operable by the user in order to change the acoustic attenuation provided by the earplug. For example, U.S. Pat. No. 6,148,821 discloses a hearing protection earplug comprising a hollow stem, which is inserted into a mating cylindrical outer opening of the shell. The hollow stem and the cylindrical wall of the outer opening of the shell both have a radially extending aperture which may be aligned by rotating the stem relative to the shell. The distal of the hollow stem is provided with a sound attenuation filter connecting the interior of the hollow stem with a sound bore within the shell communicating with the user's ear canal. When the two apertures are aligned, sound may enter through the opening into the interior of the hollow stem, pass through the filter and reach, attenuated by the filter, the ear canal.

It is an object of the invention to provide for a hearing protection earplug which comprises a shell having an outer surface individually shaped according the measured inner shape of the user's outer ear and ear canal, wherein at least one property of the earplug can be changed by a functional member engaging the shell, and wherein the earplug should be capable of being manufactured in a particularly effective manner.

It is a further object of the invention to provide for a corresponding manufacturing process.

SUMMARY OF THE INVENTION

These objects are achieved by a hearing protection earplug as defined in claim 1 and by a manufacturing method as defined in claim 36.

The invention is beneficial in that, by providing the shell with a functional member engaging the shell in a manner so as to be movable relative to the shell between a first functional position and a second functional position, with both the shell and the functional member having been produced by an additive layer-by-layer build-up process, at least one property of the hearing protection earplug is variable by movement of the functional member, so that the shell is provided with added functionality, while manufacturing of the earplug is kept particularly effective and simple, since the functional member is formed together with the shell, so that no additional assembly step for mounting the functional member at the shell is necessary.

Another aspect of the invention is a hearing protection system as defined in claim 31 and a corresponding manufacturing method as defined in claim 48. This solution is beneficial in that, by providing for a holder having a receptacle for the earplugs when not worn by the user, said holder having been produced by an additive layer-by-layer build-up process, preferably together with the shell, and said receptacle of said holder having an individual inner shape corresponding to the shape of said outer surface of said shell, the earplugs can be safely stored in the holder when not used—despite the individual shape of the shell—and the holder can be produced in a particularly efficient manner.

These and further objects, features and advantages of the present invention will become apparent from the following description when taken in connection with the accompanying drawings which, for purposes of illustration only, show several embodiments in accordance with the present invention.

BRIEF DESCRIPTION OF THE DRAWINGS

FIGS. 5A & B show a schematic longitudinal sectional view of a fourth embodiment of an earplug according to the invention, wherein the functional member is adapted to enhance the retention of the earplug within the user's ear channel, with FIG. 5A showing a disengaged state while FIG. 5B shows an engaged state;

The present invention relates to a hearing protection earplug comprising a shell which is adapted to be worn at least in part in a user's ear canal, i.e. at least a distal portion of the shell is to be inserted into the outer part of the user's ear canal, in order to provide for an acoustic attenuation, preferably of at least 10 dB averaged over the audible frequency range, when the earplug is worn by the user, in order to protect the user from excessive levels of ambient sound. The earplug may comprise an acoustic filter for adjusting the desired total acoustic attenuation or for adjusting the frequency dependent acoustic attenuation.

The shell is a hard shell having an elasticity from shore D85 to D65 and preferably is made of polyamide. In order to achieve optimized fit of the shell within the user's outer ear and ear canal, the shell has an outer surface individually shaped according to the measured shape of the user's outer ear and ear canal, i.e. the shell has an individually customized outer shape. The shape of the user's outer ear and ear canal may be determined by direct three-dimensional scanning of the ear canal and the concha or by producing an impression of the ear canal and the concha which subsequently undergoes scanning. The scanning process may be carried out optically, preferably by laser scanning.

The digital data obtained by the scanning process is then used to create the hard shell by an additive or incremental layer-by-layer build up process. Such processes are also known as "rapid prototyping". A preferred additive build-up process is a layer-by-layer laser sintering process of powder material, preferably polyamide powder. Such processes are also known as "selective laser sintering" (SLS). The basic principle therein is the repeated deposition of a thin layer of material on a surface, with the desired sectional shape then being stabilized, i.e. hardened, by laser action. Other preferred additive layer-by-layer build-up processes are laser stereo-lithography or photo-polymerization. An overview regarding additive layer-by-layer build-up processes for producing customized shells for hearing aids can be found, for example, in U.S. 2003/0133583 A1 or U.S. Pat. No. 6,533,062 B1.

According to the present invention an additive layer-by-layer build-up process is used not only for forming the outer shape of the shell in an individual manner but in addition is used to integrate a functional member within the earplug, with the functional member engaging the shell in a manner so as to be moveable relative to the shell between a first functional position and a second functional position.

In general, the shell and the functional member may be connected by an elastic portion of the shell which has a shape to enable movement of the functional member relative to the shell, or the shell and the functional member may be formed as separate parts, or the functional member may be fixedly connected to a shell at one end, with the functional member having a shape enabling movement of a portion of the functional member relative to the shell.

In some cases, the functional member will be manually operable by the user in order to enable the user to change the mechanical or acoustic set-up of the earplug as desired. However, in other cases the functional member will be operable by a change of an ambient parameter, i.e. when the ambient parameter reaches a certain threshold value. For example, the functional element in this case may be designed as an acoustic valve which automatically closes if the sound pressure level experienced by the earplug exceeds a certain limit.

In general, the functional member may be moveable axially relative to the shell and/or may be rotatable relative to the shell.

According to a first group of embodiments, the functional member may be adapted to change the outer shape of the shell when being moved from the first functional position to the second functional position: Such change of the outer shape of the shell may be used for enhancing retention of the shell within the user's ear channel. Examples of this principle are shown in FIGS. 5 to 9.

Another group of embodiments relates to the case in which the functional member is adapted to change the sound transmission through a sound passage extending through the shell, when being moved from the first functional position to the second functional position. Thereby it is possible to change the acoustic setting of the earplug, rather than changing the mechanical setting of the earplug as discussed above. Examples of this principle are shown in FIGS. 1 to 4.

Figure 10:
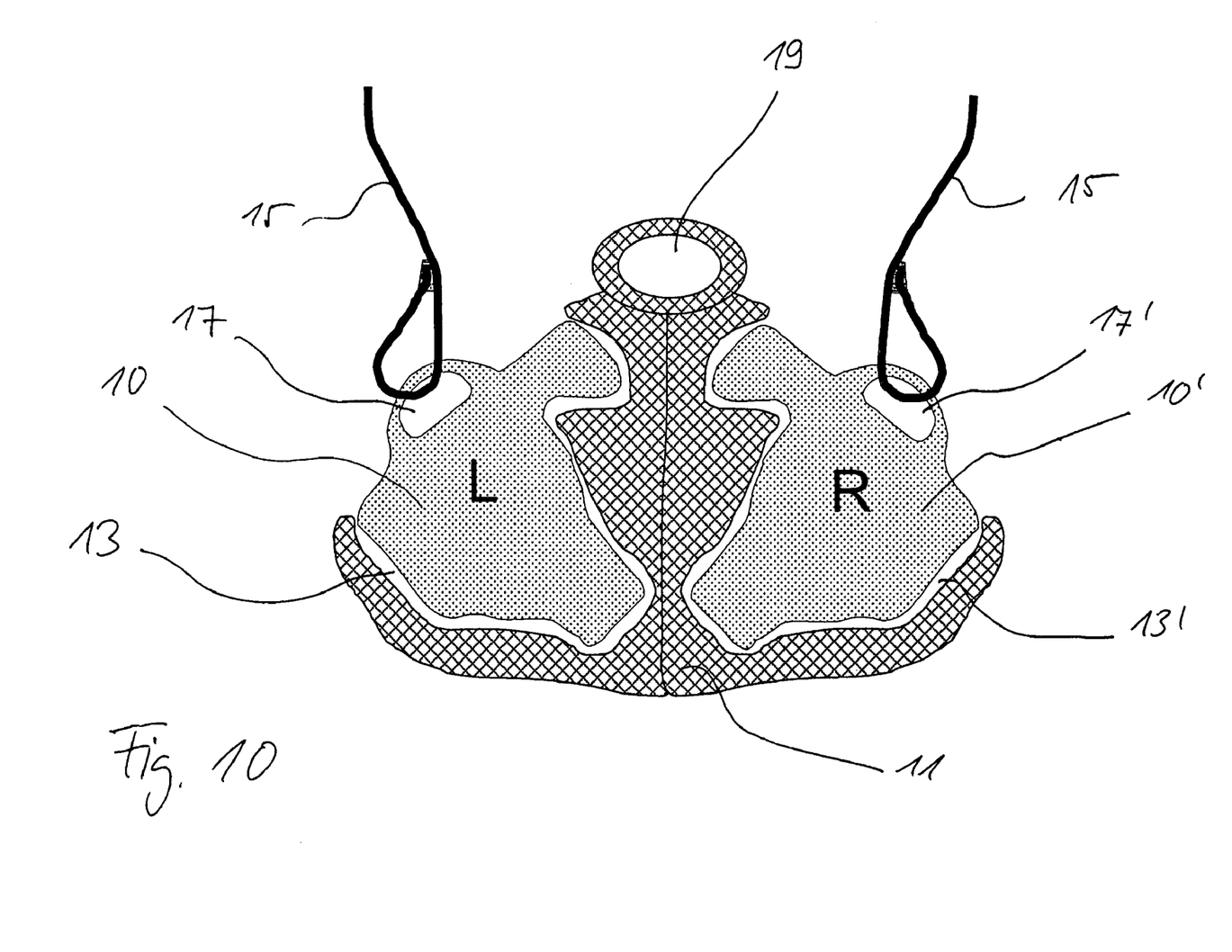
FIG. 10 shows a longitudinal sectional view of an example of a holder for carrying two customized earplugs.

According to another aspect of the invention, the additive layer-by-layer build-up process is used, rather than for forming together with the shell a functional member permanently engaging the shell, to form a holder simultaneously or subsequently with the shell, which has a receptacle for detachably receiving at least part of the earplug in order to store the earplug when not worn by the user, with the receptacle of the holder having an individual inner shape corresponding to the individual shape of the outer surface of the shell. An example of such a system is shown in FIG. 10.

Figures 1, 2:
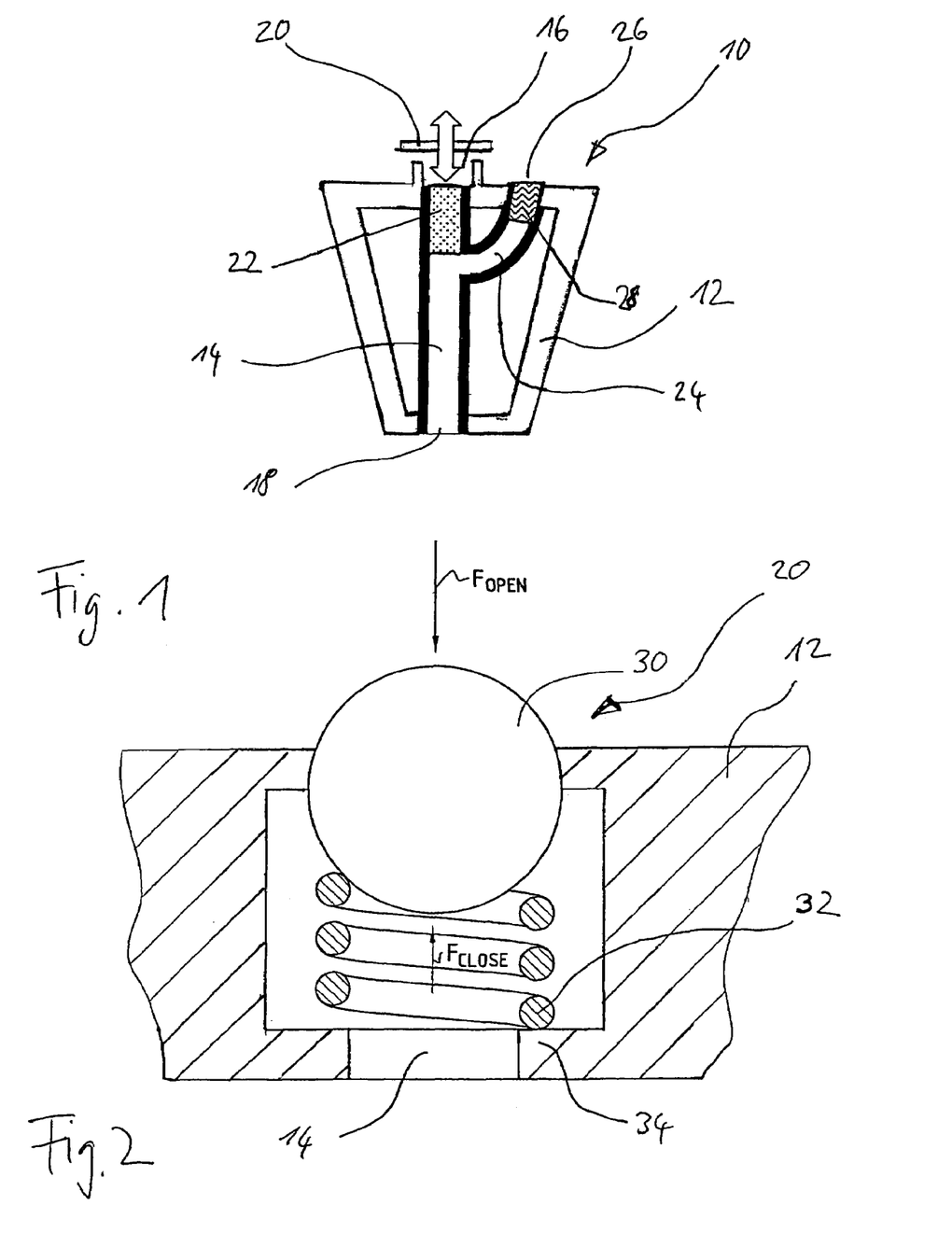
FIG. 1 shows a schematic longitudinal sectional view of a first embodiment of a hearing protection earplug according to the invention, wherein the functional member is a communication button.
FIG. 2 is a schematic longitudinal sectional view of an example of a communication button to be used in the embodiment of FIG. 1.

FIG. 1 shows a schematic longitudinal sectional view of a hearing protection earplug 10 comprising a customized shell 12 with a first sound passage 14 extending through the shell 10 from an outer sound inlet opening 16 at the outer end of the shell 10 to an inner sound outlet opening 18 at the distal end of the shell. In the outer portion of the first sound passage 14 a first passive acoustic filter 22 is provided, while an acoustic switch 20 is provided at the sound inlet opening 16. The acoustic switch 20 is moveable relative to the shell 12 between a first position in which the sound inlet opening 16 is acoustically closed by the switch 20 and a second position in which the sound inlet opening 16 is acoustically open.

The shell 12 further comprises a second sound passage 24 which extends from a second sound inlet opening 26 provided at the outer end of the shell 12 to the middle portion of the first sound passage 14, where it combines with the first sound passage 14. At the outer portion of the second sound passage 24 a second passive acoustic filter 26 is provided. The second sound inlet opening 24 is permanently open.

Preferably, the switch 20 is biased towards the closed position so that, if the switch 20 is not operated by the user, the first sound inlet opening 16 will be closed. In this mode, the acoustic attenuation provided by the earplug 10 is primarily determined by the second filter 28. When the switch 20 is operated by the user against the biasing force into the second position in order to open the first sound inlet opening 16, the second acoustic filter 28 is by-passed and the acoustic attenuation provided by the earplug 10 in this mode is primarily determined by the first acoustic filter 22, provided that the first acoustic filter 23 provides for a smaller acoustic attenuation than the second filter 28.

The function of the switch 20 may be used, for example, for enabling the user of the earplug 10 to acoustically communicate with another person when wearing the earplug 10 in a noisy environment. To this end, the first filter 22 may be designed as a low pass filter in order to attenuate high frequency noise while allowing speech frequencies to pass through. Thus the switch 20 serves as a communication button.

FIG. 2 shows a schematic example how such an integrated acoustic switch could be realized. In the construction shown in FIG. 2 the acoustic switch 120 comprises a ball 30 which fits into a corresponding outer opening provided in the shell 12, a spring element 32 for biasing the ball 30 outwardly towards the closed position and a flange 34 formed by a portion of the wall of the shell 10 for supporting the distal end of the spring element 32. Both the spring element 32 and the ball 30 are manufactured together with the shell 12 by an additive layer-by-layer build-up process and usually will be consist of the same material as the shell 12.

For opening the acoustic switch 20, the user has to press the ball 30 inwardly (i.e. downwardly in FIG. 2) against the biasing force of the spring element 32. Upon release of the ball 30, the ball 30 will automatically return into the closed position shown in FIG. 2 due to the biasing force provided by the spring element 32.

In the example shown in FIG. 2, the ball 30 and the spring element 32 are provided as parts which are completely separate from the shell 12. However, in a modified embodiment, the spring element 32 could be connected, for example at its distal end, to the shell 12 and/or even the ball 30 could be fixedly connected to the outer (proximal) end of the spring element 32. In the latter case, the ball 30 would be functionally connected to the shell 12 via an elastic part of the shell, i.e. the spring element 32. Instead of the spring element 32, for example, an elastic cantilever could be provided as the elastic biasing element.

Figure 3A:
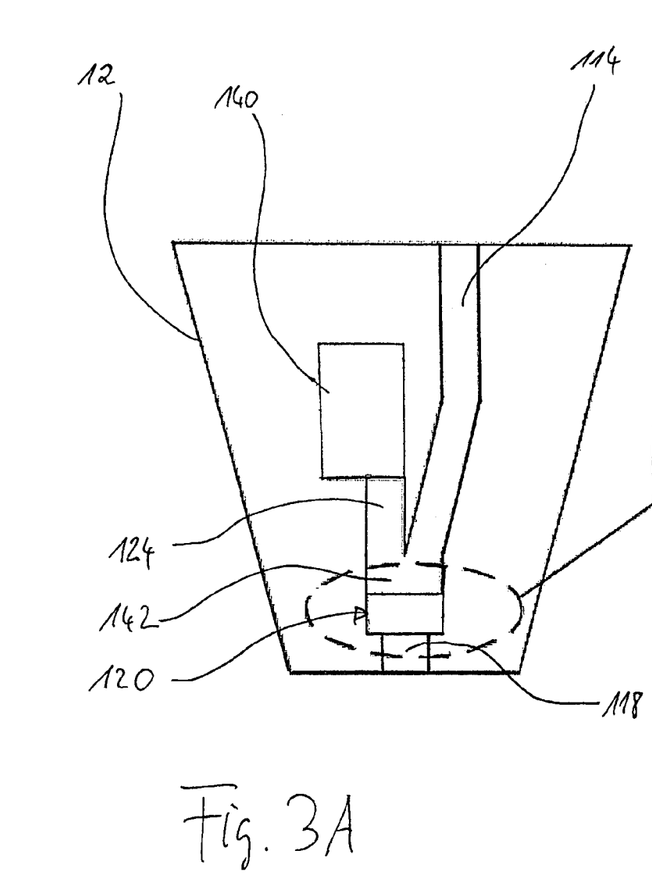
FIG. 3A is a schematic longitudinal sectional view of a second embodiment of an earplug according to the invention, wherein the functional member is designed as a mechanical peak clipper valve.
Figure 3B:
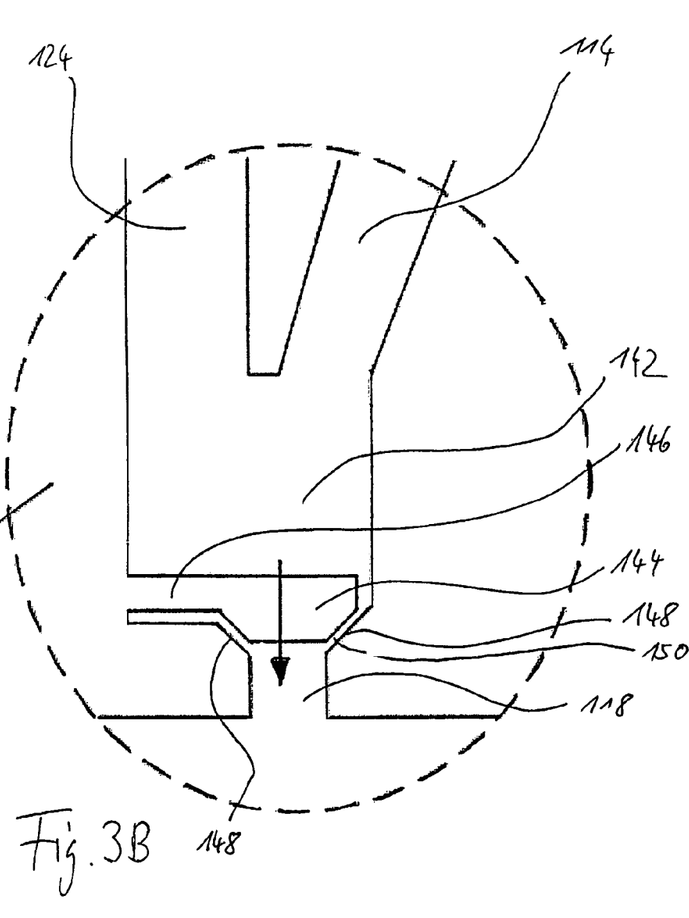
FIG. 3B shows an enlarged detailed view of the peak clipper valve of FIG. 3A.

The embodiment of FIGS. 3A and 3B is an example for the case in which the functional element is designed as an acoustic valve or switch which is not operated by the user but rather is operated automatically if an ambient parameter exceeds a certain threshold value. In the example, the functional member is designed as a valve 120 which is operable by the sound pressure level experienced by the valve 120.

The earplug shown in FIGS. 3A and 3B comprises a shell 10 including a first sound passage 114 extending from an outer sound inlet opening to a sound outlet opening 118 at the distal end of the shell 12. Further, the shell 12 comprises a second sound passage 124 which extends from a speaker 140 within the shell 12 to the distal end of the first sound passage 114, where it combines with the first sound passage 114, thereby forming a common sound output channel 142. The acoustic valve 120 is located between the sound output channel 142 and the sound outlet opening 118. The first sound passage 114 may be designed such that it primarily serves as a venting channel which does not allow significant sound transmission.

According to FIG. 3B, the valve 120 comprises a valve element 144 which is connected with the shell 12 by an integral holding portion 146 which serves to bias the valve element 144 away from a mating counter-element 148 which is likewise front integral with the shell 12. The counter-element 148 is designed like a valve seat and has an opening which forms the inner sound outlet opening 118.

In the position shown in FIG. 3B, the valve element 144 is in its open position, in which a gap 150 is left between the lower side of the valve element 144 and the counter-element 148, which serves as a sound passage for sound waves traveling from the common sound outlet channel 142 to the inner sound outlet opening 120.

If the sound pressure level within the sound channel 142 exceeds a threshold value which is primarily defined by the design of the holding portion 146 the valve element 144 is forced towards the counter-element 148 by pressure action (see arrow in FIG. 3B) so far that the lower side of the valve element 144 will rest on the counter-element 148, thus closing the sound passage gap 150, whereby sound transmission to the inner sound outlet opening 118 is prevented. Thereby it can be avoided that the user's inner ear canal experiences excessive sound pressure levels either due to excessive ambient sound pressure levels or due to excessive sound pressure levels generated by the speaker 140.

Figure 4:
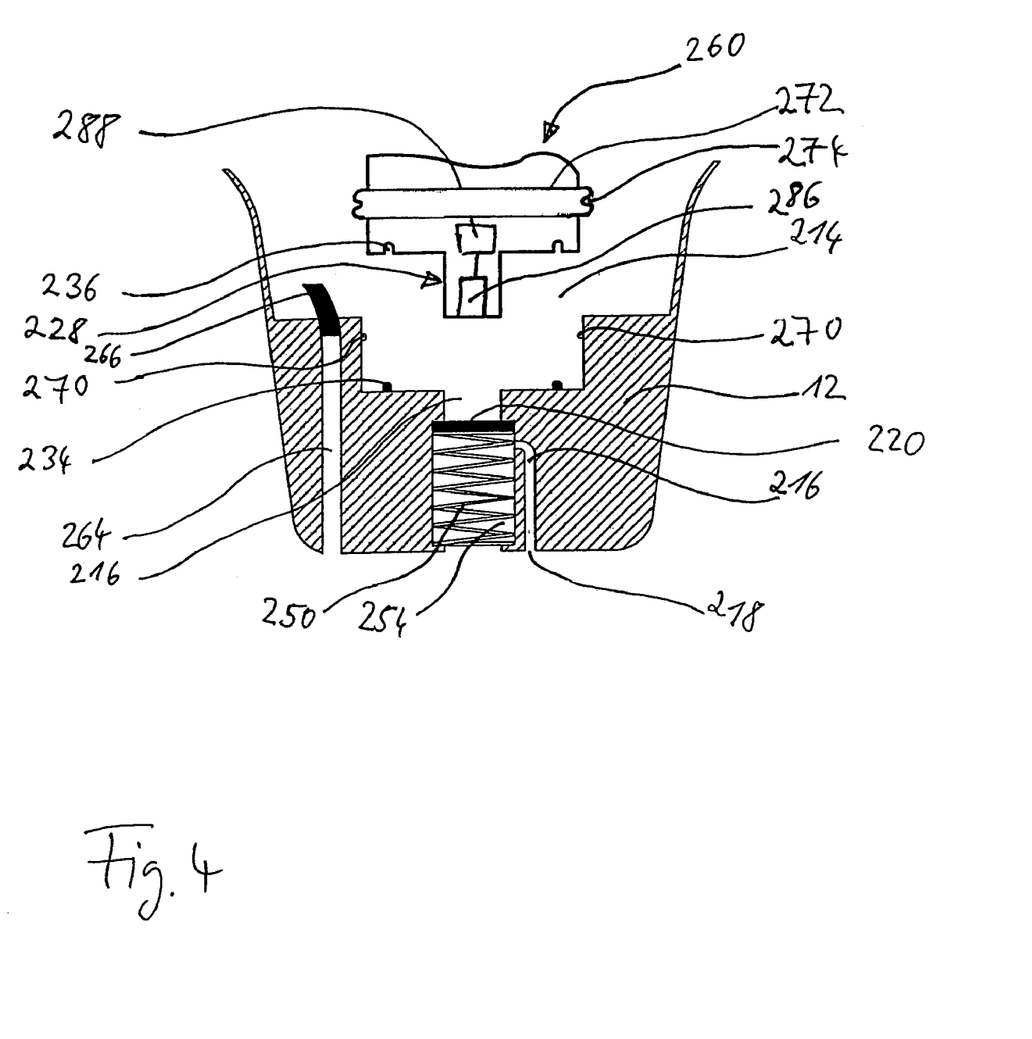
FIG. 4 shows a longitudinal sectional view of a third embodiment of an earplug according to the invention, wherein the functional member is an acoustic valve which is operated by the detachable engagement of an active unit comprising a speaker and/or a microphone with the shell.

The embodiment shown in FIG. 4 is an example for the case in which the functional member is an acoustic valve which is operated by connecting an external unit 260 to the shell 12.

The external unit 260 is designed as an active unit comprising at least one acoustic transducer 286, such as a speaker and/or a microphone at a distal projection 228 and an audio signal processor 288 connected with the acoustic transducer 286. The active unit 260 may further comprise an outer microphone (not shown) and/or an interface for communication with a remote audio signal source (not shown). The external unit 260 is adapted to be releasably insertable into an outer cavity 214 of the shell 12. To this end, in the example of FIG. 4 a resilient sealing lip 272 is provided with an external groove 274 which is adapted to engage with a radial protection 270 provided at the shell 12. The external unit 260 further comprises a groove 236 for cooperating with a mating lip 234 provided at the shell.

The shell 12 comprises a sound passage 216 extending from the outer cavity 214 to an inner sound outlet opening 218 provided at the distal end of the shell 12. Within the sound passage 216 an acoustic valve plate 220 is provided which is biased by a spring element 250 outwardly into a closed position in which the sound passage 216 is acoustically closed by engagement of the valve plate 220 with a mating surface of the sound passage 216, see FIG. 4. The spring element 250 is seated within a cavity 254 of the shell 12.

Further, the shell 12 comprises a sound channel 264 which extends through the shell and which is closed by a passive acoustic filter 266 at its outer end.

Due to the closing action of the valve plate 220, the earplug may be used as a passive hearing protection earplug when the external unit 260 is removed from the shell 12.

Upon inserting the external unit 260 into the outer cavity 214 of the shell 12, the valve plate 220 is moved into the distal direction by the distal projection 228 of the external unit 260 against the biasing force provided by the spring element 250, whereby the sound passage 216 is opened when the valve plate 220 passes the point where the angled portion of the sound passage 216 starts. In this open position of the valve plate 220 the acoustic transducer 286 provided at the distal end of the external unit 260 is acoustically connected with the distal sound outlet opening 218 via the sound passage 216, thereby enabling a communication function or a dosimeter function of the earplug.

The spring element 250 and the valve plate 220 are formed as separate parts together with the shell 12 by an additive layer-by-layer build-up process.

FIGS. 5 to 9 show embodiments which are examples for the case in which the functional member serves to change the outer shape of the shell in order to enhance retention of the shell within the user's ear canal.

Figure 5A:
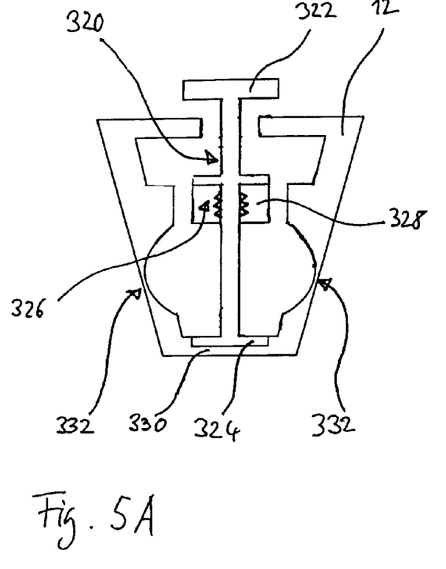
Figure 5B:
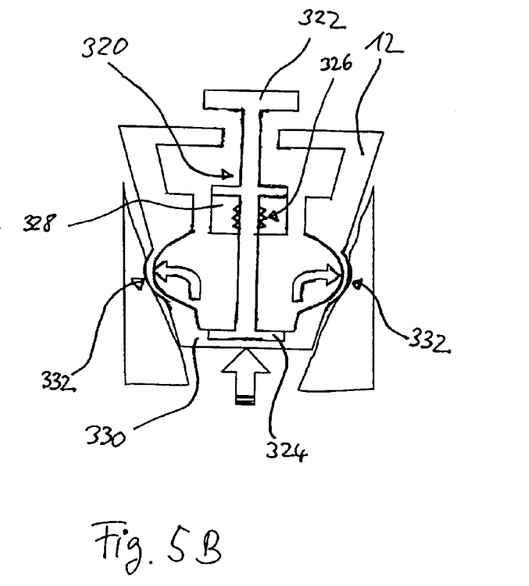

In the embodiment shown in FIGS. 5A and 5B the earplug 10 comprises a shell 12 and a functional element 320 which is formed as a shaft extending axially through the shell 12. The shaft 320 is rotatable around its longitudinal axis relative to the shell 12 by manual operation of a button 322 provided at the outer end of the shaft 320. The distal end of the shaft 320 is provided with a flange 324 which engages with the distal end of the shell 12 in such a manner that it is rotatable but not axially moveable relative to the shell 12. The middle portion 326 of the shaft 320 is in threaded engagement with an intermediate cross wall 328 of the shell 12 which extends in the transverse direction across the shell 12. Consequently, by rotating the shaft 320 relative to the shell 12 axially acting forces are applied to the shell 12 which seek to compress the shell 12 in the axial direction by moving the distal end 330 of the shell 12 towards the cross wall 328 (see arrow in FIG. 5B).

The shell 12 comprises an axial portion 332 located between the distal end 330 and the cross wall 328, which has a reduced thickness of the outer wall relative to the remainder of the shell 12 in order to enable the outer wall of the axial portion 332 to bulge outwardly upon compression in the axial direction.

In the condition shown in FIG. 5A the earplug 10 may be inserted into the user's ear canal, with the shell 12 being in an axially non-compressed state. If the user wishes to enhance retention of the shell 12 within the user's ear canal, the user may rotate the shaft 320 by manually operating the button 322 in order to axially compress the shell 12, thereby causing the axial portion 332 to bulge outwardly, with the bulged axial portion 332 acting on the inner surface of the user's ear canal in order to enhance retention of the shell 12 within the ear canal, see FIG. 5B.

The shaft 320 is manufactured as a part separate from the shell 12 by an additive layer-by-layer build-up process simultaneously with the shell 12.

Figure 6A:
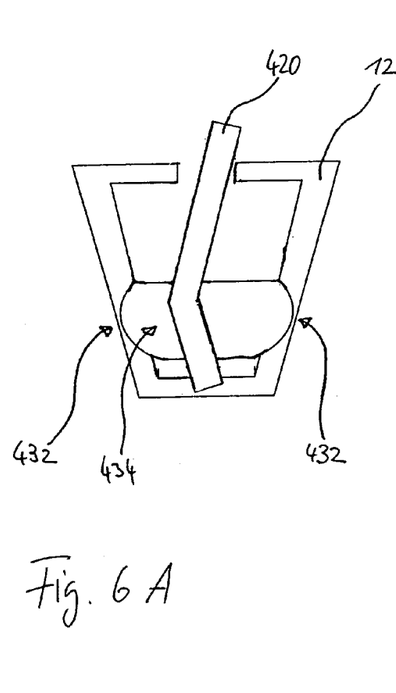
FIGS. 6A & B show views similar to FIGS. 5A and 5B, respectively, with a modified embodiment being shown.
Figure 6B:
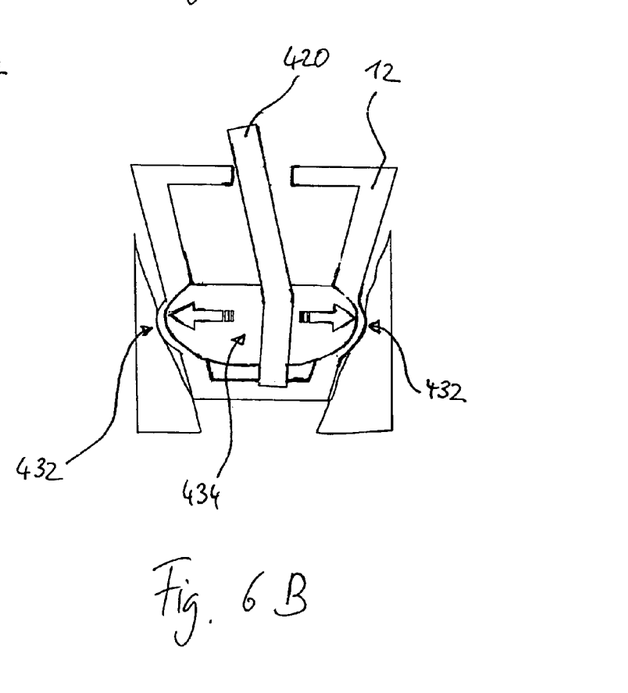

A modified embodiment is shown in FIGS. 6A and 6B. Also in this case the shell 12 has an axial portion 432 with reduced wall thickness. However, in contrast to the embodiment of FIGS. 5A and 5B the forces necessary to bulge the axial portion 432 radially outwardly are not generated by axial compression of the shell 12 but rather by an internal mechanism 434 which moves radially outwardly upon operation of a lever 420 by the user, thereby applying radially outwardly acting forces onto the axial portion 432 in order to bulge the axial portion 432 outwardly (see arrows in FIG. 6B).

The lever 420 may be rotatable around the longitudinal axis of the shell 12 and/or it may be tiltable around an axis perpendicular to the longitudinal axis of the shell 12.

Figure 7:
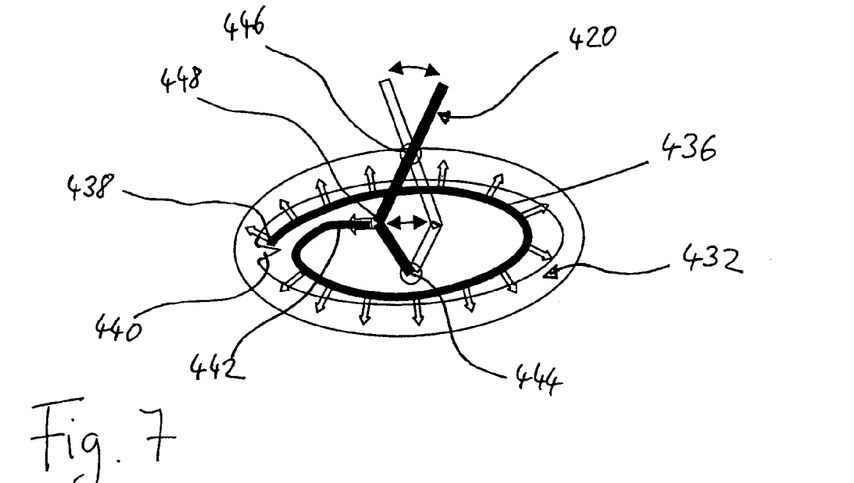
FIG. 7 to 9 show schematic perspective views of different embodiments of the functional member of the internal mechanism of FIGS. 6A and 6B.
Figure 8:
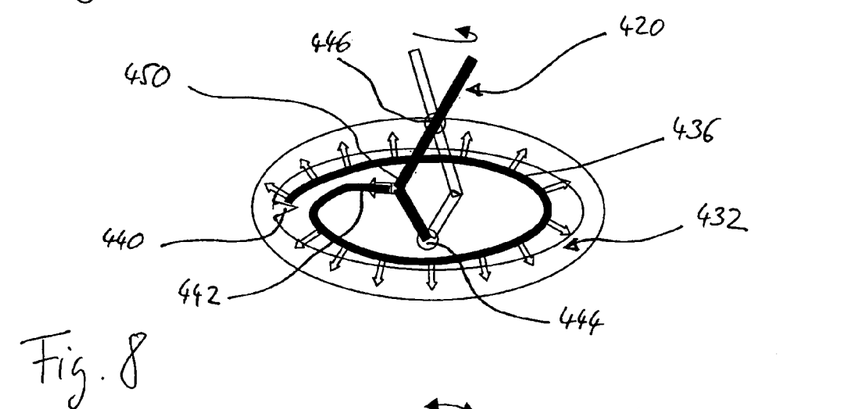
Figure 9:
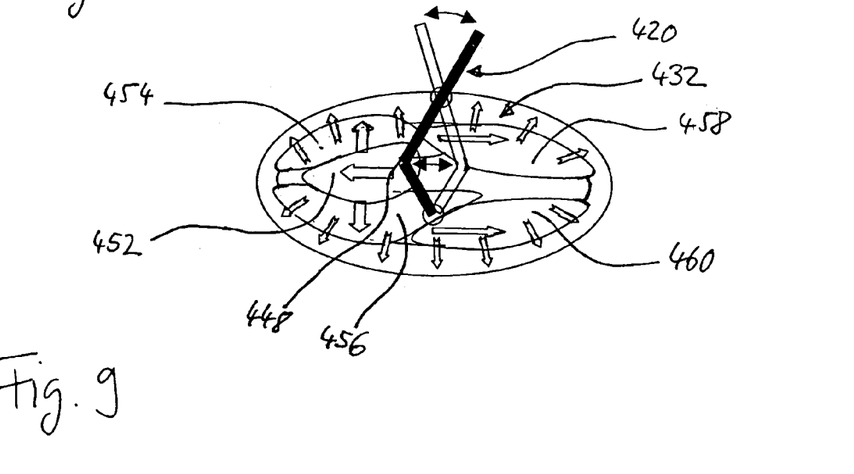

FIGS. 7 to 9 show examples of the internal mechanism 434.

In the embodiments of FIG. 7 and FIG. 8 the internal mechanism 434 comprises a spiral spring 436, with one end 438 of the spring 436 being fixed in the circumferential direction of the shell 12, for example by a corresponding stop 440 formed at the inner side of the axial portion 432 of the shell 12. Alternatively, the spring 436 could be formed integral with the shell 12. The other end 442 of the spring 436 is moveable in the circumferential direction of the shell 12 upon rotation of the lever 420 around a longitudinal axis of the shell 12 (see embodiment of FIG. 8), or the other end 442 of the spring 436 is moveable in the radial direction of the shell 12 upon tilting movement of the lever 420 around an axis perpendicular to the longitudinal axis of the shell 12 (see embodiment of FIG. 7), whereby the spring 436 expands radially outwardly towards the wall of the axial portion 432 of the shell 12 (see arrows in FIGS. 7 and 8), thereby forcing to bulge the axial portion 432 outwardly.

In both cases the lever 420 is designed as an angled lever which is supported at two axially spaced points 444 and 446. In the embodiment of FIG. 7 the lever 420 is provided with a joint 448 which allows the two angled portions of the lever 420 to pivot against each other.

In the embodiment of FIG. 8, the knee 450 between the two angled parts of the lever 420 is fixed. In the embodiment of FIG. 7 the end 442 of the spring 436 is connected to the joint 448, while in the embodiment of FIG. 8 the end 442 of the spring 436 is connected to the knee 450.

In the embodiment of FIG. 9 a tiltable lever 420 similar to that of the embodiment of FIG. 7 is provided, with the joint 448 of the lever 420 being connected to a wedge element 452 which is radially moveable by the tilting movement of the lever 420. The axial wall portion 432 comprises a first right portion 454 and a first left portion 456 which are forced outwardly away from each other upon outward radial movement of the wedge element 452, see arrows in FIG. 9. The axial wall portion 432 further comprises a second right portion 458 and a second left portion 460 which engage with the first right wall portion 454 and the first left wall portion 546, respectively, in such a manner that the wall portions and 460 are forced radially outwardly by radial outward movement of a wall portions 454 and 456, respectively, upon radial outward movement of the wedge element 452, see arrows in FIG. 9.

The wall portions 454, 456, 458 and 460 are formed integral with the shell 12, while the wedge element 452 is formed as a part separate from the shell 12 by an additive layer-by-layer build-up process.

In the embodiments of FIGS. 7 to 9, the lever 420 is formed as a part separate from the shell 12 by an additive layer-by-layer build-up process.

While the lever 420 is shown in FIG. 8 to be rotatable around the longitudinal axis of the shell, the axis of rotation of the lever 420 may be oriented at an angle between 70 and 110 degrees to the longitudinal axis of the shell.

In the representation of FIGS. 7 to 9 the lever 420 is shown in two different functional positions.

FIG. 10 shows an example of a hearing protection system comprising an earplug 10 for the user's left ear, an earplug 10' for the user's right ear and a holder 11 for storing the earplugs 10, 10' when not worn by the user. The holder 11 comprises a receptacle 13, 13' for detachably receiving one of the earplugs 10 and 10' respectively. Each earplug 10, 10' has a customized outer shape of the shell, i.e. the outer shape of the shell is determined by the measured inner shape of the user's outer ear and ear canal. Each receptacle 13, 13' is provided with an inner shape corresponding to the outer shape of the respective earplug 10, 10' in order to provide for optimized retention of the earplug 10, 10' within the associated receptacle 13, 13'. Each receptacle 13, 13' is adapted to hold the respective earplug 10, 10' by snap-fit engagement.

The two earplugs 10, 10' are mechanically connected by a flexible connection 15 which is usually worn, in order to prevent loss of the earplugs 10, 10', at the user's neck when the earplugs 10, 10' are worn in the user's ear canals. Each end of the connection 15 is connected to one of the earplugs 10, 10' by engagement with a corresponding eyelet 17, 17' provided at the outer end of the respective earplug 10, 10'.

The holder 11 is provided with an eyelet 19 by which the holder 11 may be fixed at the user's clothing.

In general, the holder 11 is formed by an additive layer-by-layer build-up process according to the measured inner shape of the user's ear canal and outer ear in order to adapt the shape of the receptacle 13, 13' to the shape the earplugs 10, 10'. Preferably the holder 11 is formed simultaneously with the earplugs 10, 10', i.e. in the same batch. Consequently, the holder 11 will be preferably made of the same material as the earplugs 10, 10' and has preferably an elasticity of between shore D85 and D65.

In general, before manufacturing the earplugs of all embodiments the inner shape of the user's ear canal and outer ear is measured and at least one earplug function according to the user's desires and needs is selected. Then, based on the measured inner shape of the user's ear canal and outer ear and on the selected earplug function, the desired individual shape of the shell and the shape of the functional member will be determined, whereupon the shell and the functional member are formed by an additive layer-by-layer build-up process simultaneously, thereby movably engaging the functional member with the shell so that the functional member may provide for the selected earplug function by being moved relative to the shell between the first functional position and the second functional position.

In general, the functional member may have a standardized shape or it may be individually shaped according to the user's individual desires and needs and/or according to the individual shape of the user's ear canal and outer ear.

Preferably, the desired earplug function is selected from a predefined list of earplug functions stored in a database. Preferably, this list includes a definition of the shape of the respective functional member associated to each of the potential earplug functions.

Preferably the earplug is adapted to enable the functional member being manually moved between the first and the second functional position when the earplug is worn in the user's ear canal. This is particularly important if the functional member is designed to provide for an enhanced retention of the shell within the user's ear canal or if the functional member is designed to change the acoustic setting of the earplug for enabling, for example, a communication function.

While various embodiments in accordance with the present invention have been shown and described, it is understood that the invention is not limited thereto, and is susceptible to numerous changes and modifications as known to those skilled in the art. Therefore, this invention is not limited to the details shown and described herein, and includes all such changes and modifications as encompassed by the scope of the appended claims.

What is claimed is:

1. A hearing protection earplug to be worn at least in part in a user's ear canal, comprising a shell having an outer surface individually shaped according to a measured inner shape of said user's outer ear and ear canal, and a functional member engaging said shell in a manner so as to be movable relative to said shell between a first functional position and a second functional position, said shell and said functional member having an elasticity of between shore D85 and D65, wherein said functional member is adapted to change the outer shape of said shell when being moved from said first functional position to said second functional position in order to provide for an acoustic attenuation of at least 10 dB averaged over an audible frequency range when worn at least in part in said user's ear canal, wherein said shell comprises an axial portion in which the thickness of an outer wall is reduced relative to a remainder of said shell in said first functional position thereof in order to cause said outer wall of said axial portion to bulge outwardly upon movement of said functional member from said first functional position into said second functional position, and wherein said functional member is adapted to axially compress said shell when being moved from said first functional position to said second functional position to produce said outward bulging of the outer wall of said axial portion.

2. The earplug of claim 1, wherein said shell and said functional member have been produced by laser sintering of a powder material, such as polyamide powder, by a laser stereo-lithography process or by a photo-polymerization process.

3. The earplug of claim 1, wherein said shell and said functional member are connected by an elastic portion of said shell, said elastic portion having a shape enabling movement of said functional member relative to said shell.

4. The earplug of claim 1, wherein said shell and said functional member are fixedly connected and wherein said functional member has a shape enabling movement of a portion of said functional member relative to said shell.

5. The earplug of claim 1, wherein said shell and said functional member are separate parts.

6. The earplug of claim 1, wherein said functional member is manually operable by said user.

7. The earplug of claim 1, wherein said functional member is rotatable around a longitudinal axis of said shell and is in threaded engagement with said shell in order to axially compress said shell upon rotation.

8. The earplug of claim 1, wherein the reduction in the thickness of the outer is due to a concavity formed at an inner side of the shell wall.

9. A hearing protection earplug to be worn at least in part in a user's ear canal, comprising a shell having an outer surface individually shaped according to a measured inner shape of said user's outer ear and ear canal, and a functional member engaging said shell in a manner so as to be movable relative to said shell between a first functional position and a second functional position, wherein said functional member is adapted to change the outer shape of said shell when being moved from said first functional position to said second functional position in order to provide for an acoustic attenuation of at least 10 dB averaged over an audible frequency range when worn at least in part in said user's ear canal, wherein said shell comprises an axial portion in which the thickness of an outer wall is reduced relative to a remainder of said shell due to a concavity formed in an inner side of outer wall in order to cause said outer wall of said axial portion to bulge outwardly upon movement of said functional member from said first functional position into said second functional position.

10. The earplug of claim 9, wherein said functional member is adapted to axially compress said shell when being moved from said first functional position to said second functional position in order to make said outer wall of said axial portion bulge outwardly.

11. The earplug of claim 9, wherein said functional element comprises or is connected to an internal element which is adapted to be forced radially outwardly towards said outer wall of said axial portion upon movement of said functional member from said first functional position to said second functional position in order to make said outer wall of said axial portion bulge outwardly.

12. The earplug of claim 11, wherein said internal element is a spiral spring element.

13. The earplug of claim 12, wherein one end of said spiral spring element is fixed in a circumferential direction of said shell, while another end of said spiral spring element is movable in said circumferential direction of said shell upon rotation of said functional member between said first functional position and said second functional position.

14. The earplug of claim 12, wherein one end of said spiral spring element is fixed in the circumferential direction of shell, while another end of said spiral spring element is movable in a radial direction of said shell upon movement of said functional member from said first functional position to said second functional position.

15. The earplug of claim 12, wherein said spiral spring element is formed integral with said shell.

16. The earplug of claim 11, wherein said internal element is a wedge element and wherein said functional member is adapted to drive said wedge element for movement in a radial direction of said shell upon movement of said functional member from said first functional position to said second functional position, said wedge element being adapted to force at least a portion of said outer wall of said axial portion radially outwardly upon movement of said wedge element in said radial direction of said shell.

17. The earplug of claim 16, wherein said wedge element is adapted for engagement with at least one first wall portion which engages with a second wall portion in such a manner that said second wall portion is forced radially outwardly by said first wall portion when said first wall portion is forced radially outwardly by said wedge element.

18. The earplug of claim 14, wherein said functional member is a lever which is rotatable around an axis oriented at an angle between 70 and 110 degrees to the longitudinal axis of said shell.

* * * * *